United States Patent [19]

Graboyes et al.

[11] Patent Number: 4,786,735

[45] Date of Patent: Nov. 22, 1988

[54] PROCESS FOR PREPARING CIMETIDINE POLYMORPH B

[75] Inventors: Harold Graboyes, Wynnewood; David S. Kirkpatrick, Broomall, both of Pa.

[73] Assignee: Smithkline Beckman Corporation, Philadelphia, Pa.

[21] Appl. No.: 77,721

[22] Filed: Jul. 27, 1987

[30] Foreign Application Priority Data

Aug. 1, 1986 [GB] United Kingdom ................. 8618846

[51] Int. Cl.$^4$ ........................................... C07D 233/64
[52] U.S. Cl. .................................................... 548/342
[58] Field of Search ......................................... 548/342

[56] References Cited

FOREIGN PATENT DOCUMENTS

| 56-104868 | 8/1981 | Japan | 548/342 |
| 1543238 | 3/1979 | United Kingdom | 548/342 |
| 2108117 | 5/1983 | United Kingdom | 548/342 |

OTHER PUBLICATIONS

B. Hegedus et al., Journal of Pharmaceutical & Biomedical Analysis, vol. 3, No. 4; pp. 303–313; 1985.

Primary Examiner—Richard A. Schwartz
Attorney, Agent, or Firm—Joseph A. Marlino; Stuart R. Suter; Alan D. Lourie

[57] ABSTRACT

A novel process for preparing cimetidine polymorph "B" comprises precipitating cimetidine from an aqueous-alcoholic solution of an acid addition salt. The precipitation is conducted at a temperature of above 15° C.

12 Claims, No Drawings

PROCESS FOR PREPARING CIMETIDINE POLYMORPH B

The present invention relates to a process for preparing cimetidine polymorph B in a substantially pure crystalline form.

Cimetidine (N-methyl-N'-cyano-N''-[2-((5-methyl-4-imidazolyl)methylthio)ethyl]-guanidine) is a potent histamine-$H_2$-receptor antagonist which has been used for a number of years in the treatment of duodenal and benign gastric ulceration, recurrent and stomal ulceration, oesophageal reflux disease and other conditions where reduction of gastric acid by cimetidine has been shown to be beneficial, for example persistent dyspeptic symptoms with or without ulceration.

It is well known (B. Hegedüs and S. Görög, J. Pharm. & Biomed. Anal. 1985, 3, 303–13) that cimetidine exhibits polymorphism, that is to say it can exist in any of a number of different crystalline forms. To date, four crystalline forms (hereinafter referred to as polymorphs) of the anhydrous base, and three polymorphs of the monohydrate of the base have been characterized. The anhydrous forms have been designated as polymorphs A–D whilst the hydrated forms have been designated polymorphs M1–M3.

It is generally recognized that substantially all formulations of cimetidine currently marketed contain polymorph A. Polymorph A can be prepared by recrystallizing cimetidine from a non aqueous organic solvent, particularly isopropanol, as described in GB No. 1,543,238. This process has been shown to be highly reproducible and to result in cimetidine which is easy to filter and has good bulk handling and formulation properties.

A method of preparing another polymorph, polymorph D (sometimes referred to as polymorph Z), has also been disclosed in GB No. 2,108,117A.

In contrast to polymorphs A and D, polymorphs B and C are disclosed by Hegedüs as being difficult to handle, due at least in part to their thixotropic properties in aqueous suspension which make separation by conventional methods such as filtration and centrifugation very difficult. This has also been the experience of the applicants up until the time of making the present invention.

Hegedüs et al further disclose that cimetidine polymorph B can be prepared by slowly cooling a hot (70°–80° C.) aqueous solution of 15% w/w cimetidine but indicate that this process is less reproducible than the known processes for preparing polymorphs A and D. A possible reason for the relatively poor reproducibility is the apparent criticality of the rate of cooling and the concentration. Thus, it is disclosed that polymorph C is obtained by rapid cooling of a hot (50°–60° C.) 5% w/w aqueous solution of cimetidine whereas polymorph M1 is obtained by pouring a hot 15% aqueous solution of cimetidine into a five fold excess of ice. The picture is further confused by the disclosure of Prodic Kojic et al, (Gazz. Chim. Italiana, 1979, 109, 539) which suggests that allowing a hot solution of cimetidine, solvent: solute ratio of 10 mls./g., to cool to room temperature gives rise to polymorph C whereas allowing solutions having solvent: solute ratios of 30 and 60 ml/g to cool under the same conditions gives rise in each instance to a mixture of polymorph M1 and polymorph B. It therefore seems likely that the problems encountered in the prior art methods for preparing polymorph B are due at least in part to contamination of the polymorph B with other polymorphs, most notably polymorph C.

In order to render possible the development of formulations comprising cimetidine polymorph B, it is necessary that there should exist a method for preparing the B polymorph which is reproducible, which gives rise to cimetidine of the required degree of polymorphic purity and is relatively easy to handle and formulate.

The process of this invention not only provides the above advantages but provides a rapid and efficient method for preparing cimetidine B using standard process equipment. The product can be easily separated by conventional techniques such as filtration and centrifugation. This is due to the fact that the polymorph B is obtained in a fluid slurry instead of a thixotropic mixture.

It has now been found that cimetidine polymorph B can be obtained in a high state of polymorphic purity, and in a form which has good bulk handling and formulation properties, by precipitating cimetidine from a solution of an acid addition salt thereof in water containing 7–20% (v/v) of a $C_{1-4}$ alcohol by addition of a base, the precipitation being conducted at a temperature above 15° C. The precipitation typically is conducted at a temperature of less than 55° C. and usually approximating to, or in excess of, ambient temperature, e.g. 20°–30° C., preferably in the range 25°–30° C. Optionally, seed crystals consisting of approximately 100% polymorph B can be added after addition of the base in order to assist the crystallization process.

On occasions, very small quantities of cimetidine C are initially formed, usually no more than 5% by weight of the total yield. These can be converted into polymorph B by ageing the suspension. Usually the suspension is aged by being held at a temperature in the range from approximately ambient temperature to about 60° C., for example in the range 40°–45° C. The suspension is maintained under such conditions until the appropriate process checks indicate that substantially all of the cimetidine is in the polymorph B form. An appropriate process check is to obtain an infra-red spectrum of the product and calculate the ratio of the peak heights of the absorbence bands at 1004 and 993 $cm^{-1}$. The concentration of polymorph C is then determined by reference to a calibration curve obtained by plotting the peak ratios for various standard mixtures of polymorph C and polymorph B. The spectral characteristics of polymorph B prepared according to the process of the present invention are set forth in Table 1.

Cimetidine polymorph B prepared according to the present process has a polymorphic purity of at least 90%, usually at least 95% and most usually in excess of 98%.

Examples of $C_{1-4}$ alcohols are methanol and isopropanol; a preferred alcohol being isopropanol. The concentration of alcohol is preferably in the range 8–15% (v/v) and most preferably is in the range 10% to 12.5%.

The cimetidine acid addition salt can be, for example, the acetate, hydrochloride, sulfate, maleate or fumarate. In order to minimize or prevent hydrolysis of the cimetidine it is preferable that the acid addition salt is formed from a carboxylic acid, and particularly preferably the acid addition salt is the acetate. The acid addition salt can be formed in situ by dissolving cimetidine base in an aqueous solution of the appropriate acid, or it can be pre-formed and simply dissolved in the aqueous phase.

The base, addition of which causes cimetidine base to precipitate, can be an inorganic base or an organic base. Examples of such bases are ammonium hydroxide, sodium hydroxide, potassium hydroxide, sodium carbonate, monomethylamine and triethylamine. Preferably the base is ammonium hydroxide. In general, sufficient base is added to adjust the pH to a value of approximately nine.

It is preferred to add the base at such a rate that precipitation of cimetidine does not occur to any significant extent until the addition of the base has been completed.

The following examples illustrate the process of the present invention but are not intended in any way to be construed as a limitation thereof.

EXAMPLE 1

To a stirred suspension of 252 grams of cimetidine form "A" in 2.0 liters of water and 250 ml of isopropanol was added a solution containing 60 grams of acetic acid in 125 ml water. The mixture was stirred and the resulting solution was clarified by filtration. To the resulting clear solution was added at room temperature, with agitation, a solution containing 68 ml of concentrated ammonia (27% w/w) in 125 ml of water. The precipitated mixture was stirred, heated to 40°–45° C., and held there for about 24 hours. The appropriate in process checks after this time indicated that the solid was completely form "B". The mixture was cooled, the product isolated by filtration, and washed with water. The solid was dried at 60° C. and yielded 240 grams (95%) of crystalline cimetidine "B" having a melting point of 142.5°–144° C.

EXAMPLE 2

| Bulk Manufacture of Cimetidine Polymorph B | |
|---|---|
| Raw materials: cimetidine | 140.0 kg |
| acetic acid | 33.3 kg |
| ammonia (SG 0.88) | 10.39 kg |
| isopropanol | 140.00 liters |
| cimetidine polymorph B seed crystals | 100.00 g. |

The cimetidine was added to an agitated solution of the isopropanol (140 L) in water (980 L) to form a slurry. A solution of acetic acid (33.3 kg) in water (70 L) was prepared and added to the slurry of cimetidine over a period of approximately 15-20 minutes, care being taken to ensure that the temperature remained in the range 25°-30° C. Following addition of the acid, the mixture was stirred for one hour to achieve complete solution. The pH of the resulting solution was approximately 5.9. The solution was then passed through a filter into another vessel.

Concentrated ammonia (SG 0.88) (10.39 kg) was added to filtered water (70 L) to give a solution of ammonium hydroxide. The resulting ammonium hydroxide solution was then added via a dip pipe into the vortex of the stirred solution of cimetidine over ca. 15-30 minutes keeping the temperature between 25° and 30° C. After addition was complete, the seed crystals were added, and the cimetidine was allowed to crystallize completely, where necessary adding water (up to 280 L in 140 L charges) if the slurry became too thick. Infra red spectral analysis of the product was then conducted in order to check the polymorphic purity, and particularly the levels of polymorph C. If there was substantially no polymorph C present, the crystalline slurry was cooled, stirred for one hour and then isolated by centrifugation. If detectable quantities of polymorph C were present, the slurry was warmed to 40°–45° C. and held at this temperature for ca. 12-20 hours or until such time as the quantity of polymorph C present was within acceptable limits. The slurry was then cooled, and the product isolated, as described above.

EXAMPLE 3

Following the procedure of Example 1 and substituting hydrochloric, sulfuric, fumaric or maleic acids for acetic acid as starting materials to form their respective cimetidine acid salts in solution and substituting mono methylamine for ammonia yields cimetidine polymorphic B.

TABLE 1

Infra-red Spectral Absorbencies of Cimetidine Polymorph B prepared according to the process of Example 1 (Spectrum obtained from a KBr Pellet) (cf Hegedus and Gorog. J. Pharm. & Biomed. Anal., 1985, 3, 303-13 Absorbence Bands (cm$^{-1}$)

| | | | |
|---|---|---|---|
| 3236 | | 1192 | |
| 3166 | | 1184 | Triplet; s.i.; m.i. |
| 3076 | | 1176 | |
| 3040 | | 1115 | |
| 2997 | | 1096 | |
| 2947 | | 1066 | |
| 2933 | | 1030 | |
| 2848 | | 1020 | |
| 2174 | s.b.; s.i. | 1004 | |
| 1604 | doublet; moderately | 993 | |
| 1587 | sharp; s.i. | 966 | |
| 1488 | | 952 | |
| 1464 | | 855 | |
| 1449 | | 839 | |
| 1429 | | 816 | |
| 1417 | | 790 | |
| 1374 | | 769 | |
| 1349 | | 743 | |
| 1306 | | 716 | |
| 1286 | | 671 | |
| 1270 | | 653 | |
| 1253 | | 644 | |
| 1236 | Triplet; s.b.; | 628 | |
| 1230 | m.i. | 423 | |
| 1219 | | | | s.b. = sharp bands
s.i. = strong intensity
m.i. = medium intensity

We claim:

1. A process for preparing cimetidine, substantially all of which is in the polymorph B form, which process comprises precipitating cimetidine from a solution of an acid addition salt thereof in water containing 7-20% (v/v) of a $C_{1-4}$ alcohol by addition of a base, the precipitation being conducted at a temperature above 15° C.

2. A process according to claim 1 wherein the $C_{1-4}$ alcohol is methanol.

3. A process according to claim 2 wherein the $C_{1-4}$ alcohol is isopropanol.

4. A process according to claim 1 wherein the alcohol is present at a concentration (v/v) of 8-15%.

5. A process according to claim 4 wherein the alcohol is present at a concentration (v/v) in the range 10-12.5%.

6. A process according to claim 1 wherein the acid addition salt is a carboxylate.

7. A process according to claim 1 wherein the acid addition salt is selected from the group consisting of acetate, hydrochloride, sulfate, maleate or fumarate.

8. A process according to claim 7 wherein the acid addition salt is the acetate.

9. A process according to claim 1 wherein the base is selected from the group consisting of ammonium hydroxide, sodium hydroxide, potassium hydroxide, sodium carbonate, monomethylamine or triethylamine.

10. A process according to claim 9 wherein the base is ammonium hydroxide.

11. A process according to claim 1 wherein the precipitation is conducted at a temperature in the range 25°–30° C.

12. A process according to claim 1 wherein a seed crystal of cimetidine polymorph B is employed.

* * * * *